United States Patent [19]
McReynolds

[11] 4,037,589
[45] July 26, 1977

[54] OCULAR SURGICAL SYSTEM

[75] Inventor: William U. McReynolds, Quincy, Ill.

[73] Assignee: William U. McReynolds, Qunicy, Ill.

[21] Appl. No.: 619,189

[22] Filed: Oct. 3, 1975

[51] Int. Cl.² .............................................. A61B 17/02
[52] U.S. Cl. .................................. 128/20; 128/303 R
[58] Field of Search ..................... 128/303 R, 341, 20, 128/325, 326, 327, 76 B, 76.5

[56] References Cited

U.S. PATENT DOCUMENTS

| | | | |
|---|---|---|---|
| 1,230,873 | 6/1917 | Crossley | 128/20 |
| 2,013,892 | 9/1935 | Lucas | 128/20 |
| 2,438,646 | 3/1948 | Pulliam | 128/20 |
| 2,701,562 | 2/1955 | Michael et al. | 128/20 |
| 2,702,540 | 2/1955 | Debeh | 128/20 |
| 2,845,925 | 8/1958 | Jayle | 128/20 |
| 3,046,988 | 7/1962 | Moreau et al. | 128/325 |
| 3,490,455 | 1/1970 | Illig | 128/303 R |
| 3,762,401 | 10/1973 | Tupper | 128/20 |
| 3,857,386 | 12/1974 | Ashbell | 128/20 |

FOREIGN PATENT DOCUMENTS

| 247,453 | 12/1969 | U.S.S.R. | 128/303 R |
|---|---|---|---|

*Primary Examiner*—Clifford D. Crowder
*Attorney, Agent, or Firm*—Lee & Smith

[57] ABSTRACT

A system for retracting and retaining the iris of the eye in a dilated position and which is composed of two basic components. The first component is a speculum for maintaining the eyelids apart and to which is attached a first retaining device. The first device has a flat, elongated shaft with one end curved so that when it is inserted through an incision in the cornea, it will engage the edge of the iris for retraction thereof. The shaft is mounted in a resilient material, such as silicone, which is encased in a metallic shell attached to the speculum. The second component is formed from a length of wire which is bent at one end to form a hook and at its other end to form a handle. A flexible shield, formed of silicone or the like, is snugly disposed about the shaft of the wire and movable between the two ends so that when the hook is inserted through a corneal incision, the shield may be held against the incision to seal it as the wire is withdrawn to retract the iris, and then retain the wire in place after desired retraction without further retention means.

15 Claims, 11 Drawing Figures

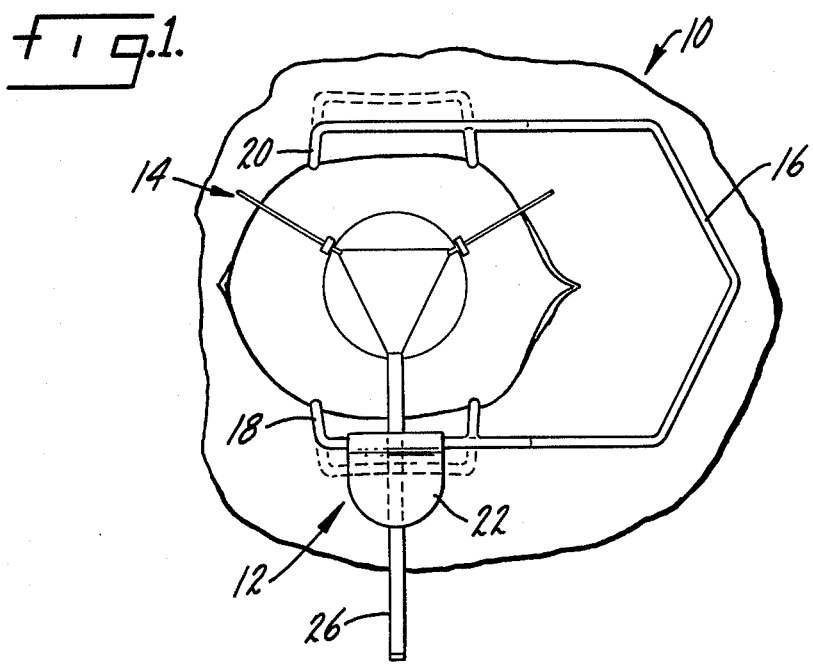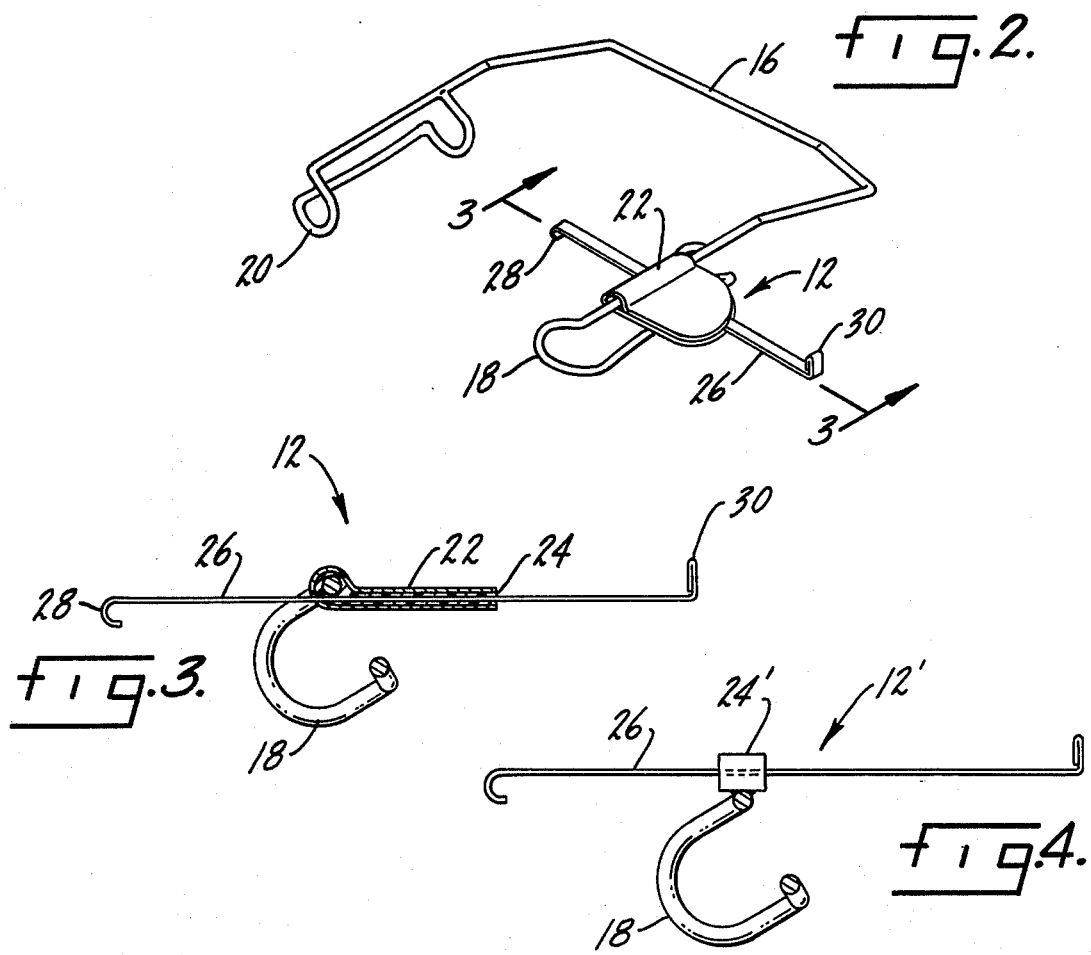

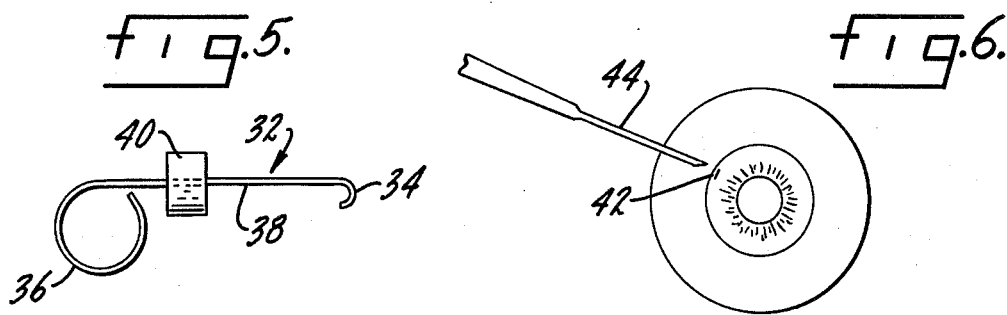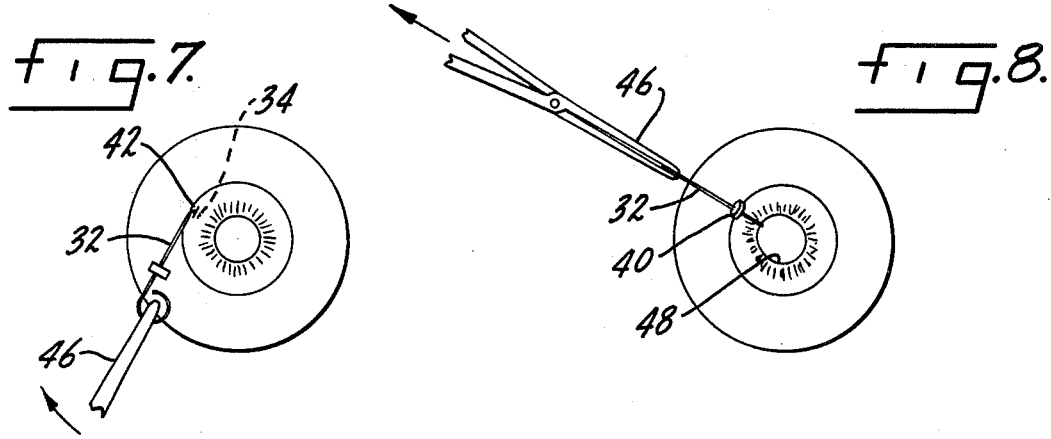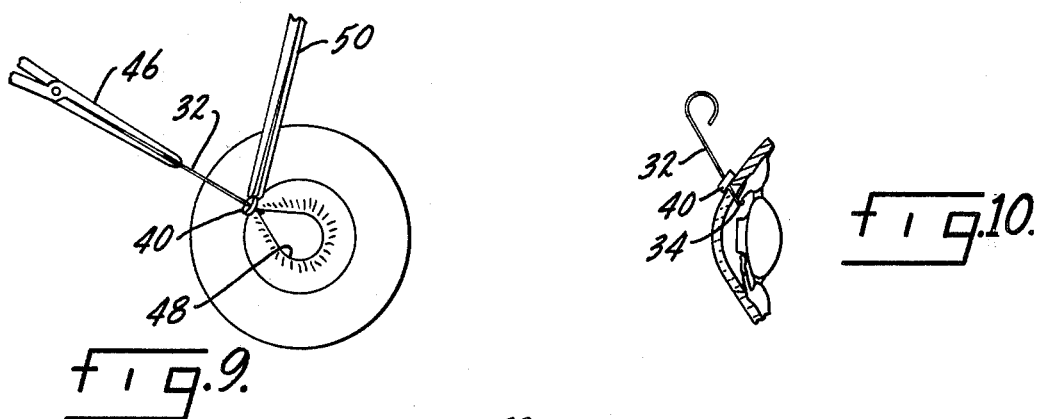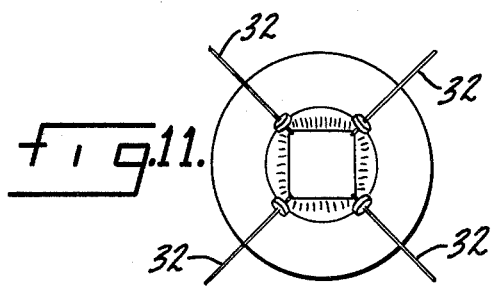

ACULAR SURGICAL SYSTEM

SUMMARY OF THE INVENTION

The Background

This invention relates to iris retractors, and more particularly to a system which retracts the iris and retains it in a desired retracted position to facilitate ocular surgery or repair beneath the iris.

During surgery, an opthalmic surgeon often requires retraction of the iris toward micro-incisions spaced about the periphery of the cornea. It is desired that devices which retract the iris do so with a minimal loss of the aqueous fluid in the eye and as unobtrusively as possible in order to interfere with the surgeon as little as necessary.

Surgical devices for retracting the iris are well-known, as exemplified by U.S. Pat. No. 3,490,455. However, such devices are inherently unuseful during the surgical procedures which require the retention of the aqueous fluid within the eye, since devices such as that illustrated in U.S. Pat. No. 3,490,455 require a relatively large incision through the cornea. Furthermore, such devices must also be fixed in position by either a suture in the eye or an elaborate mechanism combined with the wire speculum needed to hold the eyelid open. Such devices are cumbersome and time-consuming in their placement.

The Invention

These problems and others are solved according to the present invention by providing a system for retracting and retaining the iris of an eye in the dilated position which has first and second means for retracting the iris. The first means includes a shaft with a curved end for insertion within a first incision in the eye and engagement with the edge of the iris, resilient means disposed about the shaft to grip the shaft and maintain it in a fixed position, and means for maintaining the resilient means stationary in a position adjacent to the eye. The second means includes at least one length of wire having a hook formed at one end for insertion within a second incision in the eye, and a flexible shield means disposed about the shank of the wire and movable thereon to adjoin the surface of the eye to prevent the loss of aqueous fluid from the incision and to retain the length of wire in a particular position after insertion of the hook within the eye. A feature of the invention is formation of the shield from a generally flat, annular element which snugly engages the shank. The shank is generally straight, and may have a handle formed at its other end to facilitate positioning within the eye.

Preferably, the first retracting means is attached to a speculum which retains the eyelids apart during utilization of the system. The first means may comprise an elongated, flat shaft which passes through the resilient means, the resilient means being incapsulated in a container attached to the speculum.

By reason of the various features and advantages of the invention as described in detail hereafter, the surgical system according to the invention is provided which readily facilitates retraction of the iris without interfering with surgical procedures performed by the surgeon subsequent to retraction of the iris.

BRIEF DESCRIPTION OF THE DRAWINGS

An embodiment of the invention is illustrated in the following drawings, in which:

FIG. 1 is a plan view of an iris being dilated by the system according to the present invention, FIG. 2 is a perspective view of the speculum and the first means for retracting the iris, FIG. 3 is a cross section taken along lines 3—3 of FIG. 2, FIG. 4 is an alternative embodiment of the apparatus of FIG. 3, FIG. 5 is an enlarged perspective view of the second means for retaining an iris, FIGS. 6 through 10 illustrate the method of insertion of the second device within a corneal incision, and FIG. 11 is an alternative embodiment of the system according to the invention utilizing four of the second retracting means to fully retract the iris.

DETAILED DESCRIPTION OF PREFERRED EMBODIMENT

The system according to the invention is generally designated at 10 and comprises a first means 12 and a second means 14 for retracting the iris.

As illustrated in FIGS. 2 and 3, the first means 12 for retracting the iris is normally mounted on a speculum 16, although it may be mounted on any suitable device which is maintained stationary relative to the eye upon which a surgeon is operating. The speculum 16 is constructed of a resilient material, such as spring steel, and includes lid retainers 18 and 20 to hold the eyelids open during surgery, as illustrated in FIG. 1.

The first retaining means 12 is securely attached to the speculum 16, and includes a sleeve 22, preferably formed of stainless steel or another rigid material, filled with a resilient material 24, such as silicone or the like. A flat retractor 26 extends through the resilient material 24, with one end extending through an aperture in the sleeve 22 and ending in a curved end 28 utilized to retract the iris, as illustrated in FIGS. 2 and 3.

The other end of the flat retractor 26 extends from the resilient material 24, terminating in a suitable handle 30. The resilient material 24 tightly grips the flat retractor 26, but allows longitudinal movement of the retractor 26 within the sleeve 22 in order to allow retraction of the iris, as illustrated in FIG. 1.

An alternative embodiment 12' of the first retractor means is illustrated in FIG. 4. As shown, the flat retractor 26 is disposed entirely within a resilient material 24' which is immobily attached to the speculum 16. The sleeve 22 has been eliminated from this embodiment, resulting in a more flexible instrument than that illustrated in FIGS. 1-3, but utilization of a sufficiently rigid resilient material 24' will result in an instrument with holding properties similar to those of the first means 12 illustrated in FIGS. 1-3.

The first retaining means 12 is utilized as follows. The speculum 16, to which the first retaining means is attached, is used to hold the patient's eyelids open. Next, a small incision is made in the cornea in line with the flat retractor 26. The flat retractor is then inserted through the incision into the eye until the curved end 28 engages the edge of the iris. The retractor 26 lastly is withdrawn as far as desired, retracting the iris. Since the retractor is disposed within the resilient material 24, the resilient material retains the retractor, and thereform the iris, without the necessity of any further retention means.

Turning now to FIG. 5, one of the second means 14 for retracting the iris is depicted generally at 32. It comprises a length of wire, extending approximately 10 mm. or more, having formed at one end a hook 34. The hook 34 is approximately 0.25 mm. to 0.5 mm. in size, being large enough to engage the inner edge of the iris when inserted within the eye, as will be discussed further herein. The other end of the device 32 is formed into a handle 36, the handle being approximately 3 mm. in size. Of course, the handle 36 can be of any design as desired, and can be of a material diverse from that of the device 32, or very simply a non-curved extension of the device.

Between its ends, the device 32 has a substantially straight shank portion 38, with a flexible shield 40, formed of silicone or the like, tightly disposed thereabout. The shield 40 is approximately 2 mm. in diameter, and is movable along the shank 38 between the hook 34 and the handle 36.

As depicted in FIGS. 6-10, the device 32 is utilized as follows. First, a small incision 42 (drawn larger than normal for the purposes of illustration) is made in the cornea with an appropriate instrument 44. Second, the device 32 is mounted in a needle holder 46 or the like, and the hook 34 is passed through the cornea in line with the incision 42. Any loss of aqueous fluid through the incision is prevented by the shield 40 as it contacts the incision 42. Next, the hook 34 is moved centrally within the eye until it passes the edge 48 of the iris. The device 32 is then rotated approximately 90° so that the hook 34 engages the edge 48, and is then withdrawn through the incision 42 peripherally as far as desired, retracting the iris, while the shield 40 is held against the incision 42 by a suitable forceps 50. Since the shield 40 snugly engages the shank 38 of the device 32, the iris is then held in the desired position without the surgeon having to hold the instrument. By utilization of two or more of the devices 32 in combination with the first means 12, the pupil of the eye can be dilated as much as desired, and the surgeon can then proceed with any necessary operative procedure without fear of pupillary constriction and with no further attention to the iris retractors.

When utilizing the device 32, some surgeons may encounter difficulty in withdrawing the hook 34 from the interior of the eye through too small an incision 42 in the cornea. The hook 34 can be first inserted through a small needle such as a 27-gauge needle, and this assembly inserted through the cornea. The iris can then be engaged as described above and at the close of the operating procedure, when the iris is released, the hook 34 can be drawn up against the shaft of the needle and the hook and needle withdrawn together from the cornea.

As illustrated in FIG. 11, in some operative procedures, the surgeon can dispense with the first means 12 and utilize a plurality of the devices 32 to fully retract the iris.

It should be evident that the system as described above has provided a simple, yet effective means of retracting the iris of the eye for ocular surgery. Various changes can be made to the invention without departing from the true spirit thereof or scope of the following claims.

I claim:

1. A system for retracting and retaining the iris of an eye in a dilated position, comprising
   first means for retracting the iris, said first means including a shaft with a curved end for insertion within a first incision in the eye and engagement with the edge of the iris,
   resilient means disposed about said shaft to grip the shaft and maintain the shaft in a fixed position,
   means for maintaining said resilient means stationary in a position adjacent the eye,
   at least one second means for retracting the iris, said second means including a length of wire with a shank having a hook formed at one end for insertion within a second incision in the eye, and
   a flexible shield means disposed about the shank of said length of wire and movable thereon to adjoin the surface of the eye to prevent loss of aqueous fluid from the incision and to retain the length of wire in a particular position after insertion of the hook within the eye.

2. The system according to claim 1 in which said length of wire includes a handle formed at its other end.

3. The system according to claim 2 in which said shank is generally straight, and said hook and said handle form extensions of said shank.

4. The device according to claim 1 in which said shield means comprises a generally flat, annular element snugly engaged about said shank.

5. The device according to claim 1 in which said means for maintaining comprises a speculum means for retaining the eyelids apart and to which said first means is attached.

6. The device according to claim 1 in which said resilient means comprises a flexible material formed about said shaft and an encasement means for containing said flexible material.

7. A device for retracting and retaining the iris of an eye in a dilated position, comprising
   means for retaining the iris including a narrow, elongated engaging means having a curved tip for insertion within an incision in the eye and engagement with the edge of the iris,
   a substantially rigid member encasing said engaging means, said rigid member formed to permit extension and retraction only of said engaging means within said rigid member,
   means for gripping and retaining said engaging means in a fixed position within said rigid member, and
   means for maintaining said rigid member stationary in a position adjacent the eye.

8. The device according to claim 7 in which said means for maintaining comprises a speculum means for retaining the eyelids apart and to which said rigid member is immobily attached.

9. The device according to claim 8 in which said rigid member comprises a stiff sleeve and includes an aperture through which said engaging means extends.

10. The device according to claim 9 in which said stiff sleeve is wrapped about and encases a portion of said speculum means.

11. The device according to claim 7 in which said engaging means comprises a shaft and in which said means for gripping and retaining comprises a flexible material formed around said shaft.

12. A device for retracting and retaining the iris of the eye in a dilated position without the loss of aqueous fluid, comprising
   a thin, elongated member having a hook at one end for insertion within an incision in the eye and engagement with the edge of the iris, and
   shield means disposed about said member and movable between the ends of said member to adjoin the incision and prevent the loss of aqueous fluid through the incision, and to retain the member in a particular position after insertion of the hook within the eye.

13. The device according to claim 12 in which said shield means comprises a generally flat, annular element composed of a flexible material and snugly engaged about said member.

14. The device according to claim 12 in which said member comprises a length of wire with a shank shaped at said one end to form said hook and having at its other end a handle.

15. The device according to claim 14 in which the shank of said wire between said hook and said handle is generally straight, and said handle is a curved extension of said shank.

* * * * *